US00RE45936E

(19) United States
(12) Reissued Patent
Yasukochi et al.

(10) Patent Number: US RE45,936 E
(45) Date of Reissued Patent: Mar. 22, 2016

(54) PRESSURE-SENSITIVE ADHESIVE AND PATCH EMPLOYING THE SAME

(75) Inventors: Takashi Yasukochi, Tsukuba (JP); Toshiro Yamaguchi, Tsukuba (JP); Tetsuro Tateishi, Tsukuba (JP); Naruhito Higo, Tsukuba (JP)

(73) Assignee: HISAMITSU PHARMACEUTICAL CO., INC., Saga (JP)

(21) Appl. No.: 12/108,934

(22) Filed: Apr. 24, 2008

Related U.S. Patent Documents

Reissue of:
(64) Patent No.: 7,034,083
Issued: Apr. 25, 2006
Appl. No.: 10/502,474
PCT Filed: Jan. 24, 2003
PCT No.: PCT/JP03/00649
§ 371 (c)(1),
(2), (4) Date: Jul. 23, 2004
PCT Pub. No.: WO03/062342
PCT Pub. Date: Jul. 31, 2003

(30) Foreign Application Priority Data

Jan. 25, 2002 (JP) ..... JP2002/16794

(51) Int. Cl.

| | |
|---|---|
| ***C08F 8/00*** | (2006.01) |
| ***A61K 9/70*** | (2006.01) |
| ***A61K 47/04*** | (2006.01) |
| ***A61K 47/32*** | (2006.01) |
| ***C09J 4/00*** | (2006.01) |
| ***C09J 11/04*** | (2006.01) |

(52) U.S. Cl.
CPC ..... *A61K 9/7061* (2013.01)

(58) Field of Classification Search
CPC ..... C08F 8/42; A61K 9/7061
USPC ..... 525/337, 61, 328.8, 329.7
See application file for complete search history.

(56) References Cited

U.S. PATENT DOCUMENTS

| | | | | |
|---|---|---|---|---|
| 3,042,723 | A | 7/1962 | Jenkner | 568/7 |
| 3,221,745 | A | 12/1965 | Coover, Jr. et al. | 606/214 |
| 4,190,492 | A * | 2/1980 | Eckert et al. | 162/145 |
| 4,544,699 | A * | 10/1985 | Biale | 524/512 |
| 5,049,417 | A * | 9/1991 | Tsubota et al. | 427/208.6 |
| 5,344,655 | A | 9/1994 | Sakai et al. | 424/443 |
| 5,866,632 | A | 2/1999 | Hashimoto et al. | 523/118 |
| 6,511,561 | B1 | 1/2003 | Kohlhammer et al. | 156/62.2 |
| 6,953,602 | B2 * | 10/2005 | Carte et al. | 427/208.4 |

FOREIGN PATENT DOCUMENTS

| | | |
|---|---|---|
| EP | 0 965 672 A1 | 12/1999 |
| JP | 08-243377 | 9/1996 |
| JP | 11-247396 | 9/1999 |
| JP | 2001-151973 | 6/2001 |
| JP | 2002-011084 | 1/2002 |
| WO | WO 99/18136 | 4/1999 |

OTHER PUBLICATIONS

Chen Jiang, "Medical Adhesive", Adhesion in China 1996 17(1):28-30 with English translation.

* cited by examiner

*Primary Examiner* — Alan Diamond
(74) *Attorney, Agent, or Firm* — The Harris Firm

(57) ABSTRACT

An adhesive which comprises aqueous and nonaqueous polymers suitable for holding an lipophilic drug, etc., and has tackiness and cohesiveness which are sufficient for the plaster of a patch; and a patch employing the adhesive. The adhesive contains a polymer which comprises one or more kinds of acrylic or methacrylic monomer units, at least one kind of the monomer units having a hydroxy group, and which has been crosslinked with a boron compound.

14 Claims, No Drawings

PRESSURE-SENSITIVE ADHESIVE AND PATCH EMPLOYING THE SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to an adhesive that is affixed to the surface of skin so as to continuously administer a drug into a living body through the skin, and a patch employing same.

BACKGROUND ART

An adhesive layer constituting a patch normally comprises a mixture containing a drug and, as a main component, a polymer, and with regard to means for improving the tackiness and cohesiveness of this mixture, various techniques have been carried out in which a crosslinked polymer is formed by adding an appropriate crosslinking agent during the formulation process so as to gel the adhesive layer. Such an adhesive can be obtained by a method in which a drug, etc. is added to a crosslinked polymer, but in order to add a sufficient amount of drug to the adhesive layer and solve problems in molding, a method in which an appropriate crosslinking agent is added during the formulation process to a mixture containing a drug and, as a main component, a polymer so as to gel the mixture is widely employed.

Since many of the drugs used in patches are lipophilic, various types of lipophilic acrylic polymers containing substantially no water are used as the polymer constituting the adhesive layer. In recent years in particular, this type of nonaqueous patch often contains a liquid substance as a component to improve the permeability of the drug, but this further degrades the tackiness and cohesiveness of the adhesive layer, and crosslinking of the polymer is therefore a very important object.

Crosslinking of the polymer is generally carried out by a reaction between an appropriate crosslinking agent and a crosslinking functional group of the polymer. Representative examples of the crosslinking functional group include a carboxyl group, an amino group, and a hydroxy group. Thereamong, since a hydroxy group has low reactivity compared with a carboxyl group or an amino group, there might in general be less irritation of the skin such as reddening or edema caused by residual functional groups, and it might be thought that those with a hydroxy group would be suitable for application in a patch, which needs to be affixed to the skin for a long period of time.

With regard to a crosslinking agent for a hydroxy group-containing polymer, Japanese Patent No. 2967788 proposes the use of a metal chelate, a metal alcoholate, etc., but since the metal chelate and the metal alcoholate are generally highly reactive, they might decompose or denature the drug during a crosslinking reaction, and skin irritation or more serious symptoms might be caused by residual crosslinking agent.

On the other hand, an aqueous gel is conventionally formed using, for example, a borate, a silicate, or a salt of a polyvalent metal such as calcium or magnesium, which crosslinks with a hydroxy group-containing polymer under mild reaction conditions. However, these inorganic compounds have not so far been used for the preparation of a nonaqueous gel because of problems during the preparation such as the inorganic compounds generally having poor solubility in organic solvents.

An object of the present invention is therefore to solve the problems of the prior art and provide an adhesive and a patch employing same, the adhesive having sufficient tackiness and cohesiveness as the plaster of a patch and being produced from an aqueous or nonaqueous polymer that is suitable for containing an lipophilic drug, etc.

In the present description, 'nonaqueous polymer' means a polymer employing, as a solvent for the polymer, an organic solvent or a mixed solvent containing an organic solvent as a main component, and 'aqueous polymer' means a polymer employing, as a solvent for the polymer, water or a mixed solvent containing water as a main component.

DISCLOSURE OF INVENTION

As a result of an intensive investigation by the present inventors in order to solve the above-mentioned problems, it has been found that, by using as a crosslinking agent a boron-containing compound, which has conventionally been used for formation of an aqueous gel of a polyvinyl alcohol, an adhesive having sufficient tackiness and cohesiveness can be obtained from a polymer having a hydroxy group in its molecule, regardless of whether it is aqueous or nonaqueous and even when it is not a polyvinyl alcohol, and as a result of a further investigation the present invention has been accomplished.

That is, the present invention relates to an adhesive comprising a polymer containing one or more kinds of acrylic or methacrylic monomer unit, at least one of the kinds of monomer unit having a hydroxy group, and the polymer being crosslinked by a boron-containing compound.

Furthermore, the present invention relates to the adhesive wherein the boron-containing compound is boric acid or a boric acid derivative.

Moreover, the present invention relates to the adhesive wherein it contains substantially no water.

Furthermore, the present invention relates to the adhesive wherein it contains a liquid component that is compatible with the polymer.

Moreover, the present invention relates to a patch comprising the adhesive.

Furthermore, the present invention relates to the patch wherein the adhesive contains a drug.

Moreover, the present invention relates to the patch wherein it contains substantially no water.

In the present description, 'containing substantially no water' means that no water is used in the production of the adhesive or the patch, or that the adhesive or the patch that is produced contains no water.

Since the boron-containing compound as a crosslinking agent in the present invention is soluble in a hydrophilic organic solvent at a sufficient concentration, it can crosslink a polymer containing substantially no water, thus giving sufficient tackifying power and cohesive power, and thereby enabling desirable physical properties as a patch containing an lipophilic drug, a liquid component, etc. to be achieved.

MODES FOR CARRYING OUT THE INVENTION

The composition and form of the adhesive of the present invention are explained.

The crosslinkable monomer unit of the polymer contained in the adhesive of the present invention is not particularly limited as long as the unit has at least one hydroxy group.

Specific examples thereof include hydroxy group-containing acrylic monomer units such as 2-hydroxyethyl acrylate, 3-hydroxypropyl acrylate and 4-hydroxybutyl acrylate, hydroxy group-containing methacrylic monomer units such as 2-hydroxyethyl methacrylate, 3-hydroxypropyl methacrylate and 4-hydroxybutyl methacrylate, and monomer units such as vinyl alcohol, allyl alcohol, 3-buten-1-ol and 3-buten-2-ol. Among these examples, the hydroxy group-containing acrylic monomer units and the hydroxy group-containing methacrylic monomer units are preferable. 2-Hydroxyethyl acrylate is particularly preferable.

These hydroxy group-containing monomer units can be used singly or in a combination of two or more kinds.

In the present invention, either an aqueous polymer or a nonaqueous polymer can be used, and when the nonaqueous polymer is used, an acrylic polymer or a methacrylic polymer is preferably used.

The acrylic and methacrylic polymers used in the present invention are not particularly limited, and specific examples include those having as a monomer unit acrylic acid, methacrylic acid, acrylonitrile, acrylic and methacrylic acid straight-chain alkyl esters such as methyl, ethyl, propyl, butyl, pentyl, hexyl, heptyl, octyl, nonyl, decyl, undecyl, dodecyl and tridecyl esters, branched alkyl esters such as 2-ethylhexyl ester, and substituted alkyl esters such as 2-hydroxyethyl, 3-hydroxypropyl and 4-hydroxybutyl esters. One or more kinds of these monomers can be used in addition to the hydroxy group-containing monomer in the adhesive of the present invention.

It is preferable for the acrylic monomer or the methacrylic monomer to be the main component in the polymer contained in the adhesive, and the acrylic monomer or methacrylic monomer is contained at at least 30 wt % relative to the polymer, preferably 50 to 90 wt %, and particularly preferably 70 to 90 wt %.

The polymer contained in the adhesive of the present invention may contain, in addition to the hydroxy group-containing monomer and the acrylic or methacrylic monomer, one or more kinds of other monomers. Specific examples of such monomers include vinyl acetate, N-vinyl-2-pyrrolidone, itaconic acid, maleic acid, allylamine, styrene, reactive polymers (macro monomers), vinyl propionate, methylvinylpyrrolidone, vinylpyridine, vinylpiperidone, vinylpiperazine, vinylpyrazine, vinylpyrrole, vinylimidazole, vinylcaprolactam, vinyloxazole, vinylmorpholine, 2-ethylhexyl acrylate, vinylpyrrolidone, methoxyethyl acrylate and acrylic acid. 2-Ethylhexyl acrylate and vinylpyrrolidone are particularly preferable.

The polymer containing the above-mentioned monomer components, which is used in the production of the patch of the present invention, is not particularly limited as long as it contains a hydroxy group and at least one kind of acrylic or methacrylic component; it may be a polymer of a single monomer or it may be a copolymer, but a copolymer is particularly preferable. Specific examples thereof include a copolymer of 2-hydroxyethyl acrylate, 2-ethylhexyl acrylate and N-vinyl-2-pyrrolidone.

The solvent for the polymer used in production of the adhesive of the present invention can be either aqueous or organic as long as the polymer can be dissolved or made into a uniform emulsion, but a low boiling point organic solvent that can be removed by heating at 60° C. to 150° C. and that can form a nonaqueous gel is preferable, and specific examples thereof include ethyl acetate, toluene, THF, hexane, dichloromethane, chloroform, ether, methanol and ethanol.

With regard to the boron-containing compound that can be used for crosslinking of the polymer contained in the adhesive of the present invention, boric acid and derivatives thereof in which the boron is +3 valent can be cited. Examples of the boric acid derivatives include a borate and a borate ester. With regard to the borate, there can be cited chemically acceptable inorganic and organic salts whose condensation number is not limited as long as the boron is +3 valent. Specific examples thereof include sodium tetraborate and ammonium borate. Examples of the borate ester include methyl borate, ethyl borate, propyl borate and butyl borate. Boric acid is particularly preferable. These compounds can be anhydrous compounds or hydrates, but the anhydrous compounds are preferable.

These boron-containing compounds as the crosslinking agent are preferably added at 0.01 to 20 wt % relative to the total weight of the composition of the adhesive layer, and are more preferably added at 0.1 to 10 wt %, and particularly preferably 0.1 to 5 wt %, while taking into consideration the physical properties and skin irritation of the adhesive and the preparation.

The adhesive of the present invention can contain a liquid component that is compatible with the polymer; such a liquid component is not particularly limited, but an lipophilic liquid component can be cited, and it can be an absorption promoting agent, a solubilizing agent, a plasticizer, etc.

Examples of the absorption promoting agent include caprylic acid, caproic acid, lauric acid, myristic acid, palmitic acid, stearic acid, oleic acid, lauryl alcohol, myristyl alcohol, oleyl alcohol, stearyl alcohol, cetyl alcohol, methyl laurate, hexyl laurate, lauric acid dimethanolamide and isopropyl myristate.

Examples of the plasticizer include squalane, squalene, silicon oil, petroleum oil (e.g., paraffinic process oil, naphthenic process oil, aromatic process oil), and plant oil (e.g., olive oil, castor oil, camellia oil, tall oil, peanut oil).

Examples of the solubilizing agent include dipropylene glycol, glycerol, ethylene glycol and polyethylene glycol.

When the adhesive of the present invention is used in a patch, it can be integrally molded so that the adhesive includes a substrate, or the adhesive can be formed into a sheet shape that is used as an adhesive layer, and as necessary the patch comprises a support layer supporting the adhesive layer and a release paper layer provided on the adhesive layer.

The drug used in the adhesive layer comprising the adhesive of the present invention is not particularly limited as long as it can percutaneously permeate a biological membrane. Examples of the drug used in the present invention include general anesthetics, hypnotic sedatives, anti-pyretic/anti-inflammatory analgesics, steroidal anti-inflammatory agents, analeptics/stimulants, anti-motion sickness agents, agents affecting the nervous system, local anesthetics, skeletal muscle relaxants, agents for the autonomic nervous system, antispasmodics, anti Parkinsonism drugs, antihistamines, cardiotonics, antiarrhythmic agents, diuretics, antihypertensives, vasoconstrictors, vasodilators, agents for arteriosclerosis, respiratory stimulants, antitussive/expectorants, agents for treating peptic ulcers, cholagogues, hormonal drugs, agents for urogenital and anal organs, agents for parasitic skin disease, emollients, vitamin preparations, mineral preparations, hemostatics, anticoagulants, agents for liver disease, agents for habitual intoxication, agents for treating gout, agents for diabetes, antineoplastic agents, radioactive drugs, traditional Chinese preparations, antibiotics, chemotherapeutics, anthelmintics and antiprotozoan agents, and narcotics.

Examples of the antipyretic/anti-inflammatory analgesics include acetoaminophenone, phenacetin, mefenamic acid, diclofenac, fulfenamic acid, aspirin, salicylic acid, aminopyrine, alclofenac, ibuprofen, naproxen, flurbiprofen, ketoprofen, sodium amfenac, epirizole, indomethacin, pentazocine, and piroxicam; and examples of the steroidal anti-inflammatory agents include hydrocortisone, triamcinolone, dexamethasone, betamethasone, and prednisolone.

Examples of the vasodilators include diltiazem, pentaerythritol, isosorbide, trapidil, nicorandil, nitroglycerin, prenilamine, molsidomine, and tolazoline; examples of the antiarrhythmic agents include procainamide, lidocaine, propranolol, alprenolol, atenolol, nadolol, metoprolol, ajmaline, disopyramide, and mexitilen; and examples of the antihypertensives include ecarazine, indapamide, clonidine, bunitrolol, labetalol, captopril, guanabenz, mebutamate, and bethanidine.

Examples of the antitussive expectorants include carbetapentane, chloperastine, oxeladin, clobutinol, clofedanol, noscapine, ephedrine, isoproterenol, clorprenaline, methoxyphenamine, procaterol, tulobuterol, clenbuterol, and ketotifen; examples of the antineoplastic agents include cyclo-phosphamide, fluorouracil, tegafur, mitomycin C, procarbazine, doxifluridine, and ranimustine; and examples of the local anesthetics include ethyl aminobenzoate, tetracaine, procaine, dibucaine, oxybuprocaine, ambroxol, and propitocaine.

Examples of the hormonal drugs include propylthiouracil, thiamazole, metenolone acetate, estradiol, norethisterone acetate, estriol, and progesterone; examples of the antihistamines include diphenhydramine, chlorpheniramine, promethazine, cyproheptadine, and diphenylpyraline; examples of anticoagulants include potassium warfarin and ticlopidine; examples of the antispasmodics include methylatropine bromide and scopolamine; examples of the general anesthetics include sodium thiopental and sodium pentobarbital; examples of hypnotic sedatives include bromvalerylurea, amobarbital, and phenobarbital; examples of anti-epileptics include phenytoin; and examples of the analeptics and stimulants include methamphetamine.

Examples of the anti-motion sickness agents include difenidol and betahistine; examples of the agents affecting the nervous system include chlorpromazine, thioridazine, meprobamate, imipramine, chlordiazepoxide, and diazepam; examples of the skeletal muscle relaxants include suxamethonium and eperisone; examples of the agents for the autonomic nervous system include neostigmine bromide, and bethanechol chloride; examples of the anti Parkinsonism drugs include pergolide and amantadine; examples of the diuretics include hydroflumethiazide, isosorbide, and furosemide; examples of the vasoconstrictors include phenylephrine; examples of the respiratory stimulants include lobeline, dimorpholamine, and naloxone; and examples of the agents for treating peptic ulcers include glycopyrronium bromide, proglumide, cetraxate, cimetidine, and spizofurone.

Examples of the cholagogues include ursodeoxycholic acid and osalmid; examples of the agents for urogenital and anal organs include hexamine, sparteine, dinoprost, and ritodrine; examples of the agents for parasitic skin disease include salicylic acid, ciclopirox olamine, and croconazole; examples of the emollients include urea; examples of the vitamin preparations include calcitriol, thiamine, sodium riboflavin phosphate, pyridoxine, nicotinamide, panthenol, and ascorbic acid; and examples of the hemostatics include ethamsylate.

Examples of the agents for liver disease include tiopronin; examples of the agents for habitual intoxication include cyanamide; examples of the agents for treating gout include colchicine, probenecid, and sulfinpyrazone; examples of the agents for diabetes include tolbutamide, chlorpropamide, sodium glymidine, glybuzole, buformin, and insulin; examples of the antibiotics include benzylpenicillin, propicillin, cloxacillin, ampicillin, bacampicillin, carbenicillin, cephaloridine, cefoxitin, erythromycin, chloramphenicol, tetracycline, kanamycin sulfate, and cycloserine; examples of the chemotherapeutics include isoniazid, pyrazinamide, and ethionamide; and examples of the narcotics include morphine, codeine phosphate, cocaine, fentanyl, and pethidine.

These drugs can be used singly or in a combination of two or more types, and any form of the drugs such as an inorganic salt or an organic salt can of course be included. The amount of drug added is 0.1 to 30 wt % relative to the total weight of the composition of the adhesive layer while taking into consideration a sufficient permeation rate for the patch, irritation of the skin such as reddening, etc.

The adhesive layer of the patch of the present invention can contain an absorption promoting agent; the absorption promoting agent that can be used here can be any compound that is conventionally recognized to have a skin absorption promoting effect, and examples thereof include fatty acids, fatty alcohols, fatty acid esters, and ethers having 6 to 20 carbons, aromatic organic acids, aromatic alcohols, aromatic organic acid esters and ethers (those above can be either saturated or unsaturated, and can be cyclic, straight chain, or branched) and, furthermore, lactate esters, acetate esters, monoterpenoid compounds, Azone (trade name), Azone derivatives, glycerol fatty acid esters, sorbitan fatty acid esters (Span (trade name) series) polysorbate types (Tween (trade name) series), polyethylene glycol fatty acid esters, polyoxyethylene hardened castor oil types (HCO series), and sugar fatty acid esters.

Specifically, preferred examples include caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, methyl laurate, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, ethyl lactate, propyl lactate, geraniol, thymol, eugenol, terpineol, 1-menthol, borneol, d-limonene, isoeugenol, isoborneol, nerol, dl-camphor, glycerol monolaurate, sucrose monolaurate, polysorbate 20, propylene glycol, dipropylene glycol, polyethylene glycol monolaurate, polyethylene glycol monostearate, HCO-60, and 1-[2-(decylthio)ethyl] azacyclopentan-2-one (hereinafter called 'pyrrothiodecane'), and particularly preferred examples include lauryl alcohol, 1-menthol, propylene glycol, pyrrothiodecane, dipropylene glycol, and isopropyl myristate.

Such absorption promoting agents can be added at 0.01 to 60 wt %, more preferably 0.1 to 40 wt %, and particularly preferably 0.1 to 20 wt %, relative to the total weight of the composition of the adhesive layer, while taking into consideration adequate penetrability as a patch and irritation of the skin such as reddening or edema.

Moreover, as necessary, an antioxidant, a preservative, an ultraviolet-absorbing agent, and an anti-crystallizing agent can be used, and preferred examples of the antioxidant include tocopherol and ester derivatives thereof, ascorbic acid, ascorbic acid stearic acid ester, nordihydroguaiaretic acid, dibutyl hydroxytoluene (BHT), and butyl hydroxyanisole. Preferred examples of the preservative include ethyl paraoxybenzoate, propyl paraoxybenzoate, and butyl paraoxybenzoate. Preferred examples of the ultraviolet-absorbing agent include p-aminobenzoic acid derivatives, anthranilic acid derivatives, salicylic acid derivatives, coumarin derivatives, amino acid compounds, imidazoline derivatives, pyrimidine derivatives, and dioxane derivatives. As the anti-crystallizing agent, polyvinyl pyrrolidone, etc. is preferable. The total amount of such antioxidant, preservative, ultraviolet-absorbing agent, and anti-crystallizing agent can preferably be 15 wt % or less, and more preferably 10 wt % or less, relative to the total weight of the composition of the adhesive layer of the patch.

A adhesive layer having the above-mentioned composition can be produced by any method. For example, a drug-containing base composition is melted by heating, applied on a release paper or a support, and then laminated to a support or a release paper to give the present preparation. Alternatively, a drug-containing base component is dissolved in a solvent such as toluene, hexane, or ethyl acetate and spread on a release paper or a support, and after the solvent is removed by drying, the drug-containing base component is laminated to a support or a release paper to give the present preparation. Furthermore, with regard to the patch of the present invention, as long as the adhesive layer comprising the adhesive has the above-mentioned composition containing a boron-containing compound and a drug, any other kinds of configuration and starting materials for the components can be used.

For example, the patch of the present invention can comprise, in addition to the above-mentioned adhesive layer, a support layer for supporting the adhesive layer and a release paper layer provided on the adhesive layer. A stretchable or non-stretchable support can be employed as the support layer. For example, it can be selected from fabrics, nonwoven fabrics, polyurethane, polyester, polyvinyl acetate, polyvinylidene chloride, polyethylene, polyethylene terephthalate, aluminum sheet, and composite materials thereof.

The present invention is explained below in further detail with reference to Examples of the present invention, but the present invention is not limited to these Examples and can be modified in a variety of ways without departing from the scope and spirit of the present invention. In the Examples, '%' means wt % in all cases.

EXAMPLE 1

| | | |
|---|---|---|
| DURO-TAK ® (No. 387-2287) Ethyl acetate solution (solids conc.: 50%) | 4.45 g | 89% |
| Isopropyl myristate | 0.5 g (solids) | 10% |
| Boric acid [methanol solution (30 mg/mL)] | 0.05 g | 1% |
| Total | 5.0 g | 100% |

In the above composition, the DURO-TAK® (No. 387-2287, manufactured by National Starch and Chemical Company), which is an acrylic polymer, and isopropyl myristate were mixed, 2 mL of ethyl acetate was added thereto, the mixture was stirred for 1 hour, the boric acid solution was then added thereto, and the mixture was stirred for 5 minutes to give an adhesive layer solution. This was spread out on a silicone-treated surface of an 80 μm thick polyethylene terephthalate (PET) film and crosslinked at 100° C. for 15 minutes to give an 80 μm adhesive layer. As a support, a 30 μm thick sand-matted PET film was laminated so that the sand-matted surface was in contact with the adhesive layer, thus giving a matrix preparation of the present invention. After the preparation thus obtained was stored at 65° C. for 48 hours, the adhesive power was measured using a probe tack tester, and it was found that it was 102 gF, which is good. When a 25ϕ test piece was cut out and affixed to an upper arm and peeled off 2 hours later, there was no residue of the adhesive on the skin. These results suggest that the preparation obtained using the adhesive of the present invention has the perforinance of a patch that has appropriate tackiness and cohesive power.

EXAMPLE 2

| | | |
|---|---|---|
| DURO-TAK ® (No. 387-2287) | 2.9 g (solids) | 58% |
| Estradiol | 0.2 g | 4% |
| Norethisterone acetate | 0.35 g | 7% |
| Isopropyl myristate | 0.5 g | 10% |
| Polyvinylpyrrolidone | 1.0 g | 20% |
| Boric acid [methanol solution (30 mg/mL)] | 0.05 g | 1% |
| Total | 5.0 g | 100% |

In the above composition, the estradiol, norethisterone acetate, isopropyl myristate, and polyvinylpyrrolidone were mixed, 2 mL of ethanol was added thereto, the mixture was stirred for 2 hours, the DURO-TAK® and 2 mL of ethyl acetate were then added thereto and dissolved therein, and the mixture was further stirred for 3 hours until a uniform solution was obtained. The boric acid solution was added thereto and stirred for 5 minutes to give an adhesive layer solution. This was spread out in the same manner as in Example 1, and a support layer was laminated to give a matrix preparation of the present invention. After the preparation thus obtained was stored at 65° C. for 48 hours, the adhesive power of the preparation was measured using a probe tack tester, and it was found that it was 267 gF, which is good. When a 25ϕ test piece was cut out and affixed to an upper arm and peeled off 30 minutes later, there was no residue of the adhesive on the skin. The actual measurements of the drug concentrations of this preparation were 100.7% and 100.4% with respect to the initial concentrations of estradiol and norethisterone acetate, suggesting that there was substantially no decomposition of the drugs during the crosslinking reaction. Furthermore, when the stability of this preparation at 40° C. was examined, the concentrations of estradiol and norethisterone acetate after one month were 99.8% and 100.4% respectively relative to the initial concentrations, which are good results.

COMPARATIVE EXAMPLE 1

| | | |
|---|---|---|
| DURO-TAK ® (No. 387-2287) | 4.5 g (solids) | 90% |
| Isopropyl myristate | 0.5 g | 10% |
| Total | 5.0 g | 100% |

The above-mentioned composition was mixed and stirred for 1 hour to give an adhesive layer solution. A matrix preparation was obtained in the same manner as in Example 1 except that no boric acid solution was added. After the preparation thus obtained was stored at 65° C. for 48 hours, when a 25ϕ test piece was cut out and affixed to an upper arm and peeled off 2 hours later, there was residue of the adhesive on the skin.

COMPARATIVE EXAMPLE 2

| | | |
|---|---|---|
| DURO-TAK ® (No. 387-2287) | 2.95 g (solids) | 59% |
| Estradiol | 0.2 g | 4% |
| Norethisterone acetate | 0.35 g | 7% |
| Isopropyl myristate | 0.5 g | 10% |
| Polyvinylpyrrolidone | 1.0 g | 20% |
| Total | 5.0 g | 100% |

In the above composition, the estradiol, norethisterone acetate, isopropyl myristate, and polyvinylpyrrolidone were mixed, 2 mL of ethanol was added thereto, the mixture was stirred for 2 hours, the DURO-TAK® and 2 mL of ethyl acetate were then added thereto, and the mixture was further stirred for 3 hours to give an adhesive layer solution. A matrix preparation was obtained in the same manner as in Example 2 except that no boric acid solution was added. After the preparation thus obtained was stored at 65° C. for 48 hours, when a 25ϕ test piece was cut out and affixed to an upper arm and peeled off 30 minutes later, there was residue of the adhesive on the skin.

Adhesive Power Test

The adhesive power was measured as follows.

Measurement method: a 1 cm square test piece was cut out of each patch, and a tack value was measured under the conditions below using a probe tack tester (No. 1216S) manufactured by Rigaku Kogyo.

Probe: Bakelite

Adhesion time: 1 sec

Peel speed: 1 mm/sec

Load weight: 200 g

Drug Content Test

The drug content was measured as follows.

Measurement method: after a 25ϕ test piece was cut out of each patch, the release paper was removed, the total weight of the adhesive layer and the support was measured, this was placed in a 50 mL centrifuge tube, 40 mL of an acetonitrile solution and a 10 mL of a 0.05% acetonitrile solution of benzophenone as an internal standard were added thereto, and the mixture was subjected to ultrasonic extraction for 60 minutes. 0.1 mL of the extract was filtered using a membrane filter and then diluted with 0.9 mL of acetonitrile, and the drug contents of each preparation were calculated from area ratios of estradiol, norethisterone acetate, and the internal standard using high performance liquid chromatography. The preparation from which the drug had been extracted was taken out, the adhesive layer was removed from the support and dried, the weight of the support was measured, the weight of the adhesive layer was calculated, and the drug concentrations were calculated from these weights and the content of each drug.

INDUSTRIAL APPLICABILITY

A patch employing the adhesive of the present invention includes an adhesive that is formed from an aqueous or non-aqueous polymer suitable for holding an lipophilic drug, etc., and is a useful patch having sufficient tackiness and cohesiveness.

The invention claimed is:

1. An adhesive *layer* to be affixed to a skin surface, said adhesive *layer* comprising a *crosslinked* polymer consisting of one or more kinds of acrylic or methacrylic monomer unit, at least one of the kinds of acrylic or methacrylic monomer unit having a hydroxy group, and one or more kinds of other monomer unit selected from the group consisting of vinyl acetate, N-vinyl-2-pyrrolidone, itaconic acid, maleic acid, allylamine, vinyl propionate, methylvinylpyrrolidone, vinylpyridine, vinylpiperidone, vinylpiperazine, vinylpyrazine, vinylpyrrole, vinylimidazole, vinylcaprolactam, vinyloxazole, vinylmorpholine, and vinylpyrrolidone, wherein the acrylic or methacrylic monomer unit contained in the polymer is 50% to 90% by weight, the polymer is *entirely* crosslinked by a boric acid or a boric acid derivative, and substantially no water is used in production of the [adhesive] *polymer*.

[2. The adhesive according to claim 1, wherein the boron-containing compound is boric acid or a boric acid derivative.]

3. The adhesive *layer* according to claim 1, said adhesive *layer* containing a liquid component that is compatible with the polymer.

4. A patch comprising the adhesive *layer* according to claim 1 *and a support layer for supporting the adhesive layer*.

5. The patch according to claim 4[.] wherein the adhesive *layer* contains at least one drug.

6. The adhesive *layer* of claim 1 wherein the boron-containing compound is dissolved in a hydrophilic organic solvent.

*7. The adhesive layer according to claim 1 further containing at least one drug.*

*8. The adhesive layer according to claim 1 wherein said boric acid derivative is inorganic borate.*

*9. The adhesive layer according to claim 1 wherein said acrylic or methacrylic monomer unit is an acrylic or methacrylic acid ester.*

*10. The patch according to claim 4 further comprising a release paper layer provided on the adhesive layer.*

*11. An adhesive to be affixed to a skin surface, said adhesive comprising a crosslinked polymer consisting of one or more kinds of acrylic or methacrylic monomer unit, at least one of the kinds of acrylic or methacrylic monomer unit having a hydroxyl group, and one or more kinds of other monomer unit selected from the group consisting of vinyl acetate, N-vinyl-2-pyrrolidone, itaconic acid, maleic acid, allylamine, vinyl propionate, methylvinylpyrrolidone, vinylpyridine, vinylpiperidone, vinylpiperazine, vinylpyrazine, vinylpyrrole, vinylimidazole, vinylcaprolactam, vinyloxazole, vinylmorpholine, and vinylpyrrolidone, wherein the acrylic or methacrylic monomer unit contained in the polymer is 50% to 90% by weight, the polymer is entirely crosslinked by boric acid or a boric acid derivative, and substantially no water is used in production of the polymer.*

*12. The adhesive according to claim 11 wherein said adhesive contains a liquid component that is compatible with the polymer.*

*13. The adhesive according to claim 11 further containing at least one drug.*

*14. The adhesive according to claim 11 wherein said boric acid derivative is inorganic borate.*

*15. The adhesive according to claim 11 wherein said acrylic or methacrylic monomer unit is an acrylic or methacrylic ester.*

* * * * *